United States Patent
Grodzins et al.

[19]

[11] Patent Number: 6,067,344
[45] Date of Patent: May 23, 2000

[54] X-RAY AMBIENT LEVEL SAFETY SYSTEM

[75] Inventors: Lee Grodzins, Lexington, Mass.;
Suzhou Huang, Ann Arbor, Mich.;
William Wade Sapp, Melrose, Mass.;
William Adams, Powell, Ohio

[73] Assignee: American Science and Engineering, Inc., Billerica, Mass.

[21] Appl. No.: 09/203,793

[22] Filed: Dec. 1, 1998

Related U.S. Application Data

[60] Provisional application No. 60/068,172, Dec. 19, 1997.

[51] Int. Cl.[7] .................................................. H05G 1/54
[52] U.S. Cl. .......................... 378/117; 378/109; 378/110
[58] Field of Search ................................. 378/117, 108, 378/109, 110, 111, 112, 57

[56] References Cited

U.S. PATENT DOCUMENTS 5,680,430 10/1997 Khutoryansky et al. ............... 378/109

*Primary Examiner*—David P. Porta
*Attorney, Agent, or Firm*—Bromberg & Sunstein LLP

[57] ABSTRACT

A method for modulating the intensity of an x-ray beam in an x-ray inspection system so as to maintain the highest penetration power and optimum image quality subject to keeping the ambient radiation generated by the x-rays below a specified standard.

5 Claims, 1 Drawing Sheet

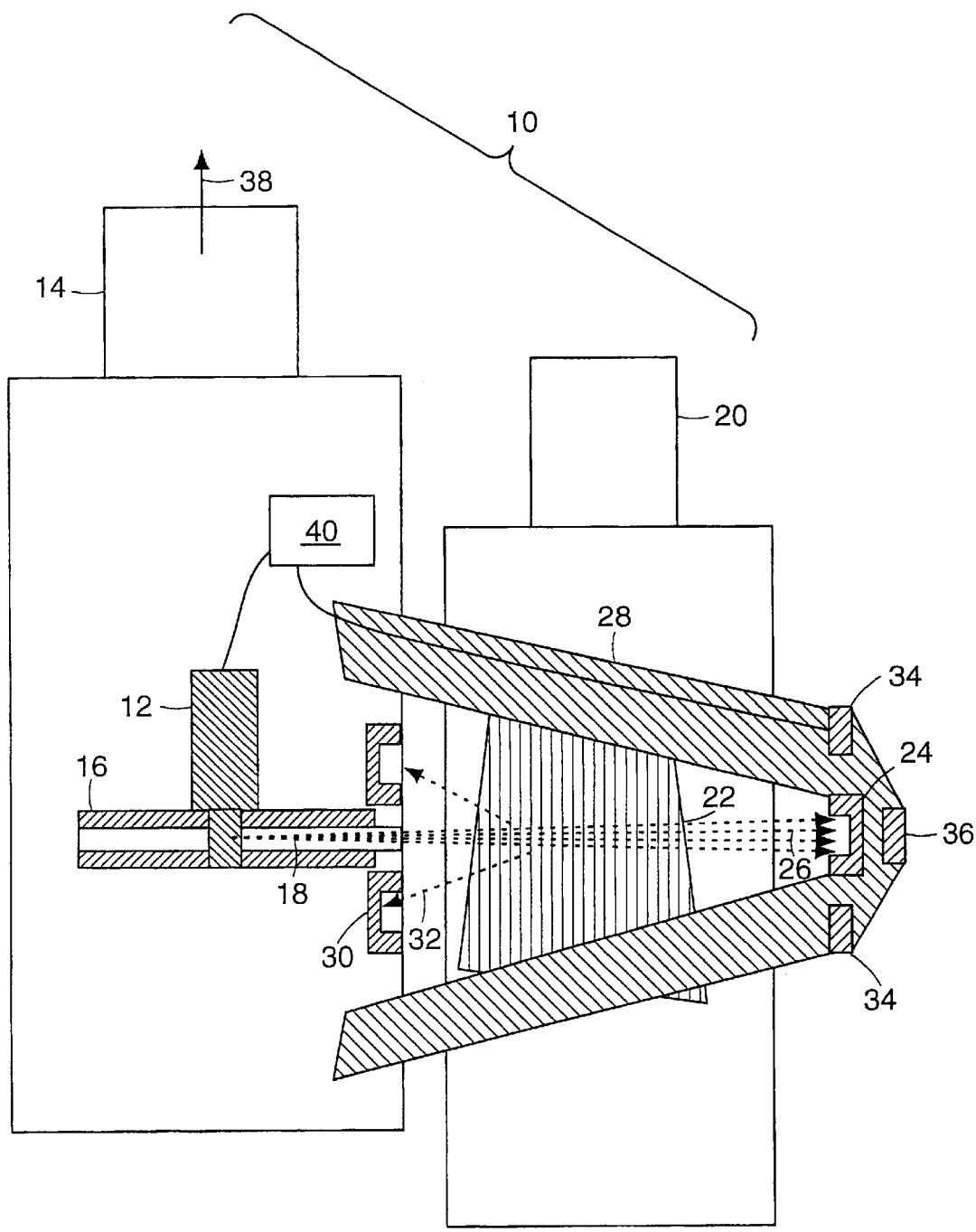

X-RAY AMBIENT LEVEL SAFETY SYSTEM

The present application claims priority from U.S. Provisional application No. 60/068,172 filed Dec. 19, 1997, which application is herein incorporated by reference.

TECHNICAL FIELD

The present invention relates to the maintenance of safe ambient levels of x-ray exposure in the presence of x-ray equipment, and, more particularly, to the active control of x-ray source characteristics based on the monitoring of ambient radiation.

BACKGROUND OF THE INVENTION

X-ray systems are commonly employed for such applications as the inspection of containers by forming a quantitative image of the intensity of the x-rays transmitted through the containers. To form the image it is necessary that the x-ray beam be characterized by photons of sufficient energy and a flux of sufficient intensity (photons per unit area per unit time) that the beam may penetrate the most heavily loaded portions of the container undergoing inspection, and deliver sufficient intensity to the detectors of the transmitted beam that adequate signal-to-noise may be achieved during the scan time so that images of adequate quality may be obtained. For a given energy distribution of x-rays, the flux is tantamount to the x-ray power in the beam.

Safety of personnel requires that ambient levels of x-ray radiation fall below prescribed limits. Under the inspection scenario described above, a heavily loaded container gives rise to the lowest levels of ambient radiation since the contents of the container strongly absorb the x-ray beam, and minimal x-ray energy is scattered into the ambient environment of the x-ray system. However, if the container is only lightly loaded, ambient radiation may increase substantially.

If both the characteristic energy of the x-ray beam and its power are maintained constant, then the system must be shielded to account for the empty-container "worst case" level of ambient radiation, substantially adding to the requisite weight and cost of the system. In some cases, the requisite weight of the shielding drives the energy and power of the x-ray generator and hence the performance of the system. This may be the case, for example, for hand-held portable x-ray systems.

Current cargo systems operate at a maximum energy and at power levels complying with U.S. Government radiation requirements of a so-called "Cabinet System." That classification allows mobile inspection systems, for example, to be used with minimal restrictions in congested areas, a feature so highly desirable as to be a requirement that the Government imposes on the mobile x-ray systems it purchases. In order to use higher peak energies than are commonly employed, the x-ray intensity may modulated so that the highest intensity consistent with a Cabinet System is always maintained. In that way, a heavily loaded truck may be inspected with a beam intensity that is orders of magnitude greater than that used (or necessary) when the inspected truck is lightly loaded.

The control of x-ray beam intensity is well known in the art, and is used, for example, for reducing the dynamic range of intensity incident on radiation detectors in the face of intervening material, and for reducing, or evening out, the heat load on the anode of the x-ray source.

SUMMARY OF THE INVENTION

In accordance with one aspect of the invention, in one of its embodiments, there is provided a system for limiting, to a prescribed limit, exposure to ambient penetrating radiation produced by an apparatus having a source of penetrating radiation. The system has at least one monitor detector for producing a signal related to ambient penetrating radiation scattered by the object and detected by the monitor detector and a controller for limiting at least one of the maximum energy of the beam and the beam flux on the basis of the signal produced by the at least one monitor detector. In accordance with alternate embodiments of the invention, the monitor detector may be disposed on a side of the object distal to the source of penetrating radiation or exterior to the object and at a non-zero radial distance from the beam of penetrating radiation. The monitor detector may also be disposed in line with the beam of penetrating radiation.

BRIEF DESCRIPTION OF THE DRAWING

The foregoing features of the invention will be more readily understood by reference to the following detailed description taken with the accompanying drawing in which FIG. 1 provides a schematic top view of an x-ray system employing ambient radiation level control in accordance with a preferred embodiment of the present invention.

DETAILED DESCRIPTION OF PREFERRED EMBODIMENTS

The invention will be described in terms of a preferred embodiment as applied, without limitation, to a mobile x-ray system for the inspection of trucks, as described in U.S. patent application Ser. No. 08/799,533, filed Feb. 12, 1997, and hereby incorporated by reference. In this application, the mobile x-ray inspection system moves past stationary containers such as trucks and produces x-ray images of the contents of the containers.

Referring to FIG. 1, a schematic top view is shown of an x-ray inspection system designated generally by numeral 10. A source (or generator) 12 of penetrating radiation, typically x-rays, is enclosed within mobile unit 14, which may be a truck, by way of example. Scanning mechanism 16, which may be a wheel with hollow spokes or another scanning mechanism known to persons skilled in the art, forms an x-ray beam 18 that scans the inspected container 20, shown here, by way of example, as a truck. Container 20 holds cargo 22 which is traversed by x-ray beam 18. At least one detector 24 is disposed on the side of (container 20 distal to source 12 for detecting radiation 26 transmitted through cargo 22 and container 20. Detector 24 may be mounted, for example, on a boom 28 that straddles the inspected container 20. Other elements of an x-ray inspection system shown in FIG. 1 include backscatter detectors 30 for detecting radiation 32 scattered by cargo 22 in the backward direction. Additionally, in accordance with a preferred embodiment of the invention, ambient radiation monitor detectors 34, which may be attached to boom 28, monitor forward scattered ambient radiation. A monitor detector 36 may be disposed posterior to transmission detector 24 for measuring radiation passing through detector 24.

Radiation monitor detectors 34, having response times typically faster than 1 ms, are disposed at one or more points around system 10. The electrical output of radiation monitor detectors 34 is used to modulate the parameters of x-ray generator 12 so as simultaneously to maintain the maximum penetrating power and the acceptable ambient radiation levels. Thus, the radiation shielding necessary to maintain acceptable levels of ambient x-ray radiation may be reduced while maintaining the power of the x-rays to penetrate the inspected objects and to provide the required quality of x-ray images.

While the invention is described with only the beam intensity being modulated, it should be understood that in some instances it may be more effective to modulate the energy of the x-ray beam, by varying the accelerating potential applied between the cathode and anode of the x-ray source, as known to persons of ordinary skill in the x-ray art. Similarly, design considerations may dictate the modulation of both the energy and the intensity. Any modulation of source parameters on the basis of detected ambient radiation is within the, scope of the present invention.

In typical operation, mobile unit 14 carries out an inspection of container or truck 20, which remains stationary, by moving in forward direction 38 with boom 28 and detector 24 of transmitted radiation straddling the container. As x-ray beam 18 scans truck 20, monitor 36 and transmission detector 24 monitor the strength of the transmitted radiation. Detectors 34 on the side of boom 28 monitor the scattered radiation.

In a preferred embodiment of the invention, transmission detector 24 serves as the master governor, with monitor detectors 36 and 34 serving as secondary. generally "safety-net" detectors. The electrical outputs from detectors 24, 34, and 36 am direct measures of the energies deposited in them, that is, of the radiation levels at the detectors. The radiation levels at each of detectors 24, 34, and 36 are preferably calibrated periodically, using procedures well-known in the art, against radiation standards for quantitative assessment of ambient radiation.

In response to the electrical outputs of detectors 24, 34, and 36, controller 40 varies the intensity of x-ray beam 18, for example, by changing the electron beam current that impinges on the anode of x-ray generator 12. Commercial x-ray tubes use a gridded electron gun whose output can be rapidly changed over orders of magnitude by changing the electrical potential on the grid. This simple approach is used in accordance with a preferred embodiment of the invention, although other methods of modulating the energy and flux of x-ray beam 18 in response to measured ambient radiation levels are within the scope of the invention.

In accordance with one embodiment of the invention, the calibrated outputs of the detectors 24, 34, and 36 are sent to a comparator circuit, contained within controller 40 for determining which detector has the higher reading and for producing an output voltage from that highest-reading detector that is fed to the gridded x-ray tube so as to maintain the ambient radiation at or below the regulatory limit.

To illustrate an advantage which may be obtained by employing the present invention, one may consider a mobile x-ray inspection system examining a cargo containing bars of steel 7" thick. A beam of 1 MeV photons is attenuated by about a factor of 10,000 on passing through the steel and a beam power of about 1 kW power is typically needed to penetrate the steel and obtain a useful image of the truck in a few minutes. As the examination proceeds, there comes a point when the x-ray beam reaches the end of the steel bars and the beam intensity striking the detector increases by that factor of 10,000. The ambient radiation is now orders of magnitude greater than the regulatory limits. In the standard technique in which the x-ray beam parameters are fixed, these regulatory limits would govern the allowable beam intensity and that would effectively prevent the steel from been examined. In this invention, the signed from the transmission detector is fed back to reduce the beam intensity, by a factor of 10,000 if necessary. That reduced beam intensity is still sufficient to examine the nearly empty container. The ambient radiation may exceed the regulatory limits for only the time it takes to affect the change in intensity, which is generally much shorter than a millisecond.

The described embodiments of the invention are intended to be merely exemplary and numerous variations and modifications will be apparent to those skilled in the art. All such variations and modifications are intended to be within the scope of the present invention as defined in the appended claims.

We claim:

1. A system for limiting, to a prescribed limit, exposure to anbient penetrating radiation produced by an apparatus having a source of penetrating radiation for producing a beam of penetrating radiation, the beam having a maximum energy and a beam flux, the penetrating radiation being incident upon an object, the system comprising:

a. at least one monitor detector for producing a signal related to ambient penetrating radiation scattered by the object and detected by the at least one monitor detector; and b. a controller for limiting at least one of the maximum energy of the beam and the beam flux on the basis of the signal produced by the at least one monitor detector.

2. A system according to claim 1, wherein the at least one monitor detector is disposed on a side of the object distal to the source of penetrating radiation.

3. A system according to claim 1, wherein the at least one monitor detector is disposed exterior to the object and at a non-zero radial distance from the beam of penetrating radiation.

4. A system according to claim 1, wherein the at least one monitor detector is disposed in line with the beam of penetrating radiation.

5. A method for limiting to a prescribed limit exposure to ambient penetrating radiation produced by an apparatus having a source of penetrating radiation for producing a beam of penetrating radiation, the beam having a maximum energy and a beam flux, the penetrating radiation being incident upon an object, the method comprising:

a. detecting ambient penetrating radiation scattered by the object; and b. limiting at least one of the maximum energy of the beam and the beam flux on the basis of the of the signal produced by the at least one monitor detector.

\* \* \* \* \*